United States Patent
Zorn

(10) Patent No.: US 9,228,927 B2
(45) Date of Patent: Jan. 5, 2016

(54) FIELD TESTING APPARATUS AND METHOD FOR DETERMINING THE DYNAMIC ELASTIC MODULUS OF ASPHALT

(71) Applicant: Bernd Zorn, Haemerten (DE)

(72) Inventor: Bernd Zorn, Haemerten (DE)

( * ) Notice: Subject to any disclaimer, the term of this patent is extended or adjusted under 35 U.S.C. 154(b) by 84 days.

(21) Appl. No.: 13/851,578

(22) Filed: Mar. 27, 2013

(65) Prior Publication Data

US 2014/0026635 A1 Jan. 30, 2014

(30) Foreign Application Priority Data

Jul. 30, 2012 (DE) ...................... 20 2012 007 351 U

(51) Int. Cl.
| | |
|---|---|
| G01N 3/00 | (2006.01) |
| G01N 3/30 | (2006.01) |
| G01N 3/24 | (2006.01) |
| G01N 3/303 | (2006.01) |
| G01N 33/42 | (2006.01) |

(52) U.S. Cl.
CPC .. G01N 3/30 (2013.01); G01N 3/24 (2013.01); G01N 3/303 (2013.01); G01N 33/42 (2013.01)

(58) Field of Classification Search
None
See application file for complete search history.

(56) References Cited

U.S. PATENT DOCUMENTS

| 5,313,825 | A | 5/1994 | Webster et al. | |
|---|---|---|---|---|
| 2007/0131025 | A1 * | 6/2007 | Kinast et al. | 73/84 |

FOREIGN PATENT DOCUMENTS

| DE | 202005018879 U1 | 2/2006 |
|---|---|---|
| DE | 10 2007 035 348 A1 | 2/2009 |
| DE | 102007035348 A1 | 2/2009 |
| DE | 102008035565 A1 | 2/2010 |
| DE | 202010009539 U1 | 9/2010 |

OTHER PUBLICATIONS

Jaehnig, Dipl.-Ing., AL Sp-Asphalt 09, Research Institute for Roads and Transportation, Issue 2009, pp. 10-16, FGSV Verlag, Koeln, Germany.

* cited by examiner

*Primary Examiner* — Lisa Caputo
*Assistant Examiner* — Brandi N Hopkins
(74) *Attorney, Agent, or Firm* — Cohen & Hildebrand, PLLC

(57) ABSTRACT

Field testing apparatus includes load device with drop weight for generating force impact and load stamp for introducing the force impact into asphalt. Load stamp is guided in a guide element. The load stamp is guided with its stamp face resting flat on the asphalt surface for testing. Time dependence of acceleration of load stamp is measured with acceleration sensor and movement of the load stamp is measured with displacement sensor. When impact force generated by the device is applied, the load stamp penetrates into the asphalt for testing. This penetration has a dynamic and a static depth ($s_{dyn}$, $s_{st}$). Load stamp is subjected to force impacts: For each force impact, time dependence of acceleration of load stamp and movement of load stamp are measured and temporarily stored, until static penetration depth ($s_{st}$) is smaller than or equal to the predetermined minimum static penetration depth ($s_{stmin}$).

14 Claims, 3 Drawing Sheets

Figure 1:
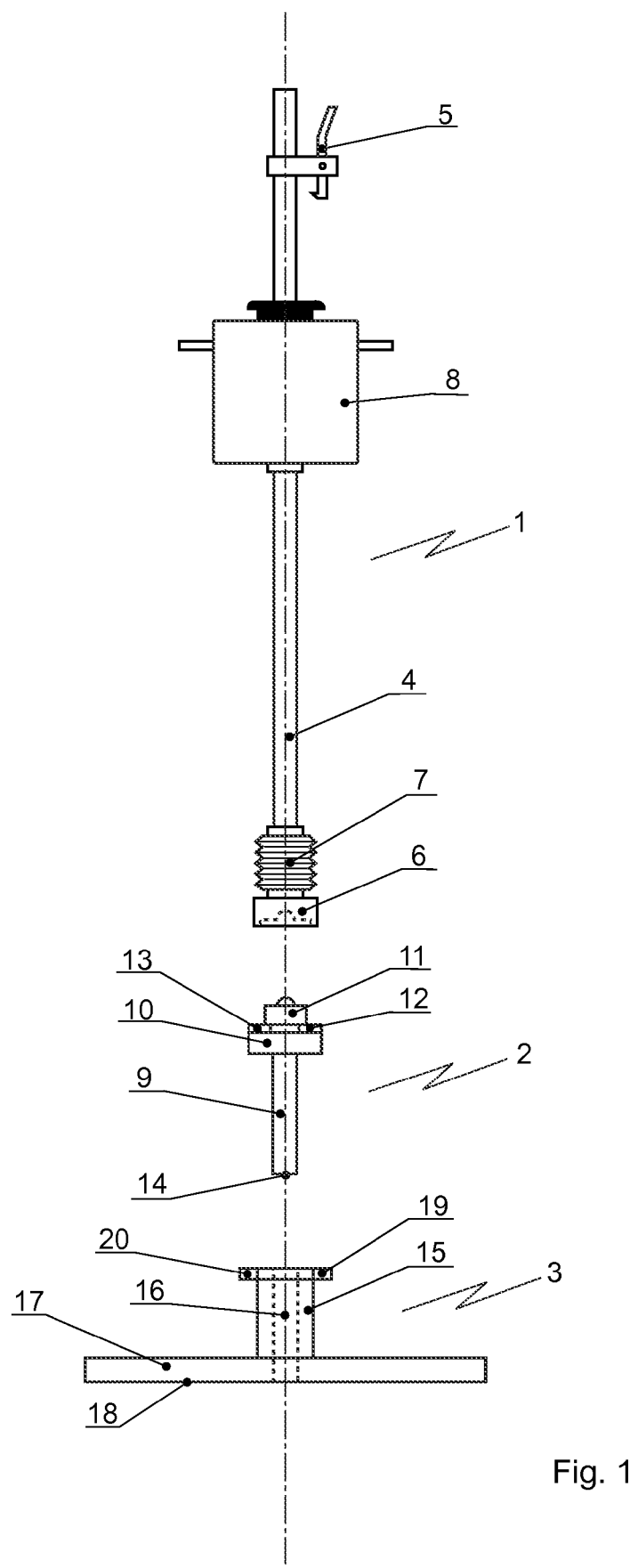

FIELD TESTING APPARATUS AND METHOD FOR DETERMINING THE DYNAMIC ELASTIC MODULUS OF ASPHALT

BACKGROUND OF THE INVENTION (1) Field of the Invention

The invention concerns a field testing apparatus and a method for determining the dynamic elastic modulus of asphalt. A preferred field of application of the invention is the determination of the dynamic elastic modulus of asphalt in asphalt poured as pavement or as installed asphalt.

The dynamic elastic modulus of asphalt poured as pavement or as installed asphalt is typically determined in accordance with the splitting tension-swelling test. For this purpose, a cylindrical test specimen is taken from the asphalt layer to be tested, to which a sinusoidal pressure swelling load is introduced via two diametrically opposite load input rails arranged on the outer surface of the cylindrical specimen (see operating instructions for determining the stiffness and fatigue behavior of asphalts with the splitting tension-swelling test as input variable for the dimensioning, AL Sp-asphalt 09, Research Institute for Roads and Transportation, Issue 2009, pp. 10-16). The tensile stress produced in the test specimen causes significant material fatigue and ultimately the fracture of the test specimen.

The test specimen is loaded with a force-controlled, harmonized sinusoidal swelling load without load pauses at different stress levels and load frequencies, wherein the load is continuously applied and increased until macro cracks appear in the test specimen. The test force and the deformation of the test specimen transverse to the direction of the test force are detected. The dynamic elastic modulus is calculated from these values. When the dynamic elastic modulus increases of under repeated loading of the test specimen, the curve of the dynamic elastic modulus as a function of the number of applied loads is a measure for the stiffness of the asphalt; conversely, a decrease of the curve of the dynamic elastic modulus as a function of the number of loads is a measure for the fatigue behavior of the asphalt. The splitting tension-swelling test is complicated and can only be performed in the laboratory, so that test results are available only after a considerable time after the samples have been removed and are related to permanent damage in the asphalt surface to be tested due to the sample removal. This test is therefore not suitable as a field test.

(2) Description of Related Art

DE 10 2008 035 565 A1 mentions that the load carrying capacity of asphalt in an uncured state can be determined by using a device with a drop weight according to technical test method TP BF-StB Part B 8.3. In particular, the dynamic elastic modulus, in DE 10 2008 035 565 A1 called dynamic deformation modulus, of the test plenum is determined. A drop weight tester according to the above test method includes a load plate having a diameter of 300 mm and a mass of 15 kg, and a load device composed of drop weight, guide rod, spring element and release device. The mass of the drop weight is 10 kg, the total mass of the guide rod is 5 kg. The drop weight acts on the load plate with a force of 7.07 kN. An acceleration sensor, which is configured to measure the movement of the load plate placed on the test plenum that is caused by the force impact of the drop weight, is coupled to the load plate. The dynamic elastic modulus of the test plenum is determined from the movement of the load plate, i.e. from the movement of the test plenum caused by the force impact. However, the determined dynamic elastic modulus is not a specific characteristic value of the asphalt in the asphalt layer, but rather a characteristic value that describes the dynamic behavior of the entire system of the layer structure below the test plenum, i.e. of the compacted soil, the support layers built on top of the compacted soil and the final layer of asphalt. This drop weight cannot be used to determine the dynamic elastic modulus as a characteristic material parameter of the asphalt in the asphalt layer.

BRIEF SUMMARY OF THE INVENTION

Starting from the aforementioned prior art, it is an object of the present invention to provide a field testing apparatus and a method for determining the dynamic elastic modulus of asphalt, which delivers test results quickly, i.e. without the time delay caused by sampling and laboratory testing. In addition, handling of the field testing apparatus and carrying out the method should not cause any or only insignificant permanent damage in the asphalt surface to be tested.

This object of the invention is attained with a field testing apparatus having the features of claim 1, and with a method having the features of the claim 6. The claims 2 to 5 recite advantageous embodiments of the field testing apparatus. Claims 7 and 8 recite advantageous embodiments of the method for determining the dynamic elastic modulus by using an advantageous field testing apparatus according to claims 4 and 5.

A field testing apparatus according to the invention for determining the dynamic elasticity modules of asphalt include a load device composed of a guide rod with an attached release device, a drop weight, a spring element and a detachable cap, and load stamp with a substantially cylindrical stamp shaft, with a stamp face being formed on one end face of the stamp shaft and a stamp head being formed on the other end face of the stamp shaft. The stamp face is oriented transversely to the longitudinal axis of the stamp shaft. The elements of the load device are designed and arranged such that one end of the guide rod is terminated by the detachable cap and the release mechanism is arranged on the guide rod in the region of the opposite end of the guide rod. The spring element is arranged on the side of the detachable cap pointing in the direction of the guide rod. The drop weight has preferably a central through-opening through which the guide rod passes. The drop weight is arranged so as to be able to freely slide between the release mechanism and the spring element along the guide rod. The field testing apparatus further includes a guide element with a support surface that can be placed on an asphalt surface and with a through-opening terminating in this support surface. The through-opening and the stamp shaft of the load stamp are configured and arranged to correspond to one another so that the stamp shaft can pass and move longitudinally through the through-opening, with its stamp face being oriented towards the support surface. The load stamp can move far enough inside the through opening in the guide element in the longitudinal direction so that the stamp face can protrude beyond the support surface. The stamp head of the load stamp has a support plate to which the detachable cap of the load device can be non-positively coupled so that a force impact can be transferred from the detachable cap to the load stamp, namely in the longitudinal direction of the stamp shaft. An acceleration sensor constructed to measure the time dependence of the acceleration of the load stamp is affixed to the load stamp. A displacement sensor is arranged on the guide element for detecting the longitudinal movement of the load stamp in the through-opening of the guide element.

In a preferred embodiment of the field testing apparatus, a support plate with a support surface is arranged on one end of the guide element, wherein the support surface of the support plate forms one end of the guide element and is oriented perpendicular to the longitudinal axis of the guide element. The support plate enables secure positioning of the guide element to substantially prevent slipping on the asphalt surface to be tested and consequently also of the stamp face of the load stamp on the asphalt surface.

Preferably, the guide element is designed as a guide tube and the load stamp is designed as a circular cylinder with a circular stamp face.

In an advantageous embodiment of the aforedescribed embodiment of the invention, the circular stamp face of the load stamp has a diameter of 10 mm to 60 mm, preferably 30 mm. The drop weight has a mass of 8 kg to 20 kg, preferably 10 kg. The drop height of the drop weight is selected by positioning the release device on the guide rod such that the drop weight acts on the load stamp with a force of 5 kN to 15 kN, preferably 6.28 kN.

According to another advantageous embodiment, the acceleration sensor and the displacement sensor may be connected with a radio module for wirelessly transmitting the measured curves and values to an electronic storage and evaluation device. The measured curves and values are preferably transmitted to the storage and evaluation device by radio transmission. The radio module of the displacement sensor is advantageously mounted on the guide element, whereas the radio module of the acceleration sensor is advantageously mounted on the load stamp.

For determining the dynamic elastic modulus of asphalt, the asphalt is first adjusted to a temperature between 40° C. to 60° C. The support surface of the guide element is placed and positioned on the asphalt surface to be tested. The load stamp is inserted into the through opening of the guide element, such that the stamp face of the load stamp just barely rests on the asphalt surface and the load stamp can be moved in the guide element vertically in relation to the asphalt surface. The load device is operatively connected to the load stamp, meaning that it is coupled to the load stamp by placing the detachable cap of the load device on the support plate of the load stamp, thereby enabling a force impact generated with the load device is transmitted to the stamp shaft in the longitudinal direction. The drop weight is raised against the action of gravity along the guide rod to a raised position, and locked with the release device. The guide rod is oriented approximately vertically. The spring element is at the bottom end of the guide rod in relation to the effective direction of gravity, i.e. near the coupling point between the load device and the load stamp, and rests on the contact cap. The drop weight is released and moves due to the effect of gravity in an accelerated movement along the guide rod in the direction the coupling point between the load device and the load stamp. The drop weight strikes the spring element at the lower end of the guide rod. Upon impact on the spring element, a force impact is generated, which is transmitted to the load stamp so as to act in the longitudinal direction of stamp shaft. The force impact is introduced into the asphalt via the stamp face of the load stamp. The load stamp penetrates into the asphalt accompanied by an elastic deformation and optionally by a permanent deformation of the asphalt. The time dependence of the acceleration of the load stamp is detected by the acceleration sensor and temporarily stored. The movement of the load is detected by a displacement sensor and is also temporarily stored. The static penetration depth of the stamp shaft of the load stamp into the asphalt to be tested is determined from the movement of the load stamp and compared with a predetermined minimum static penetration depth. When the determined static penetration depth is greater than the predetermined minimum static penetration depth, an additional force impact is produced with the load device at the same position of the asphalt surface, as described above. The time dependence of the acceleration and the movement of the load stamp are measured and temporarily stored, and the static penetration depth of the stamp shaft into the asphalt to be tested caused by this repetitive force impact is determined and compared with the predetermined minimum static penetration depth. Additional force impacts are generated at the same position and introduced into the asphalt to be tested until the determined penetration depth of the stamp shaft into the asphalt to be tested caused by the last of the respective repeated force impacts is less than or equal to the predetermined penetration depth. A total penetration depth of the movement of the stamp shaft of the load stamp caused by this last force impact into the asphalt to be tested is computed from the time dependence of the acceleration of the load stamp caused by this force impact, which has resulted in a static penetration depth less than or equal to the predetermined minimum static penetration depth, by integrating twice and subsequently forming the maximum value. The static penetration depth determined from the movement of the stamp shaft is then subtracted from this total penetration depth. The remaining penetration depth is the dynamic penetration depth of the stamp shaft due to this most recent force impact which caused a static penetration depth that is smaller than or equal to the predetermined minimum static penetration depth. The dynamic elastic modulus is calculated from this dynamic penetration depth.

In the preferred embodiment of the field testing apparatus with a load stamp having a circular stamp face, the dynamic elastic modulus is determined according to the equation $$E_d = 2*(1-\mu^2) \cdot F/\Pi *r*s_{dyn}$$

with
 $E_d$=dynamic elastic modulus
 $\mu$=Poisson's ratio for asphalt=0.25
 F=force impact
 r=radius of the stamp face.

With the equally preferred and advantageous design of the field testing apparatus with a circular stamp face of the load stamp having a diameter between 10 mm and 60 mm, preferably of 30 mm, a mass of the drop weight of between 8 and 20 kg, preferably 10 kg, and by positioning the drop weight at a drop height which causes a force impact between 5 kN and 15 kN, preferably 6.28 kN, to be transmitted to the load stamp when the drop weight strikes the spring element, the predetermined minimum static penetration depth has a value ≤0.15 mm, preferably ≤0.1 mm.

BRIEF DESCRIPTION OF THE SEVERAL VIEWS OF THE DRAWING(S)

Figure 2:
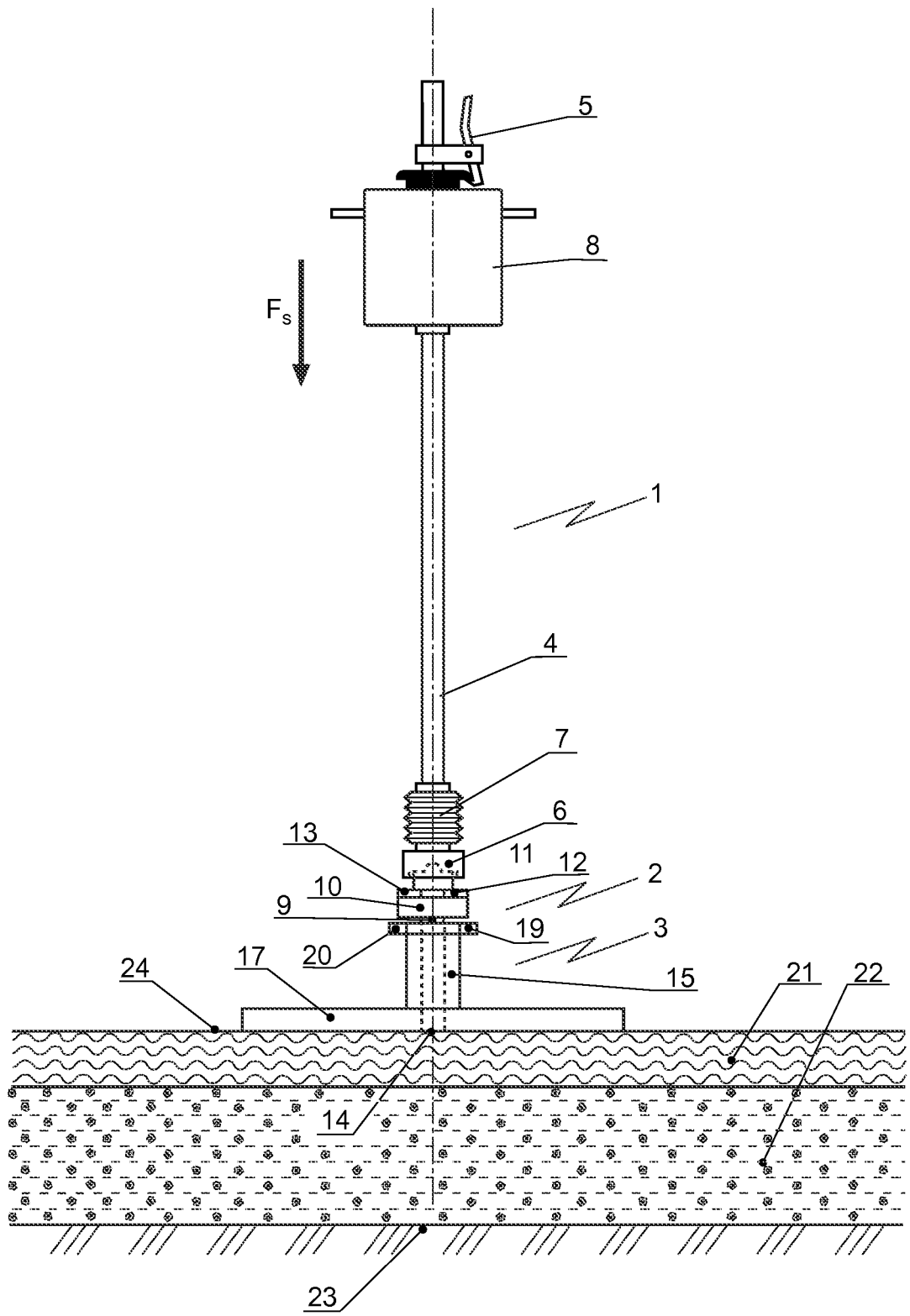
Figure 3A:
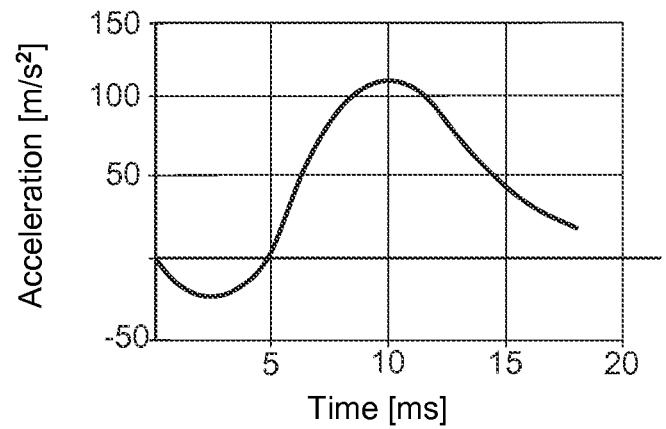
Figure 3B:
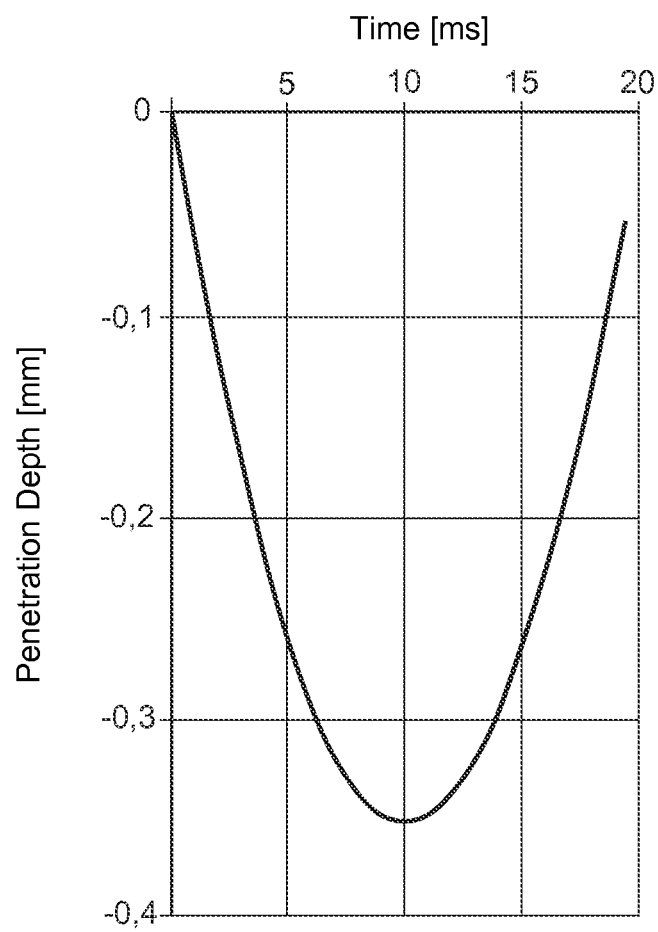

The invention will now be explained in more detail with reference to the following exemplary embodiment. The respective drawings show in:

FIG. 1 a schematic diagram of a field testing apparatus,

FIG. 2 a field testing apparatus placed and positioned on an asphalt surface and prepared for a test procedure, FIG. 3a a curve of the measured time dependence of the acceleration of the load stamp, and FIG. 3b a curve of the time dependence of the penetration depth of the load stamp into the asphalt to be tested determined by a two-time integration.

DETAILED DESCRIPTION OF THE INVENTION

FIG. 1 shows the basic structure of a field testing apparatus composed of a load device 1, a load stamp 2 and a guide element 3 for determining the dynamic elastic modulus $E_d$ of asphalt, wherein the aforementioned components 1 to 3 are each shown separately. The load device 1 has a guide rod 4 with a release mechanism 5, a detachable cap 6 with a spring member 7 resting thereupon, and a drop weight 8. The detachable cap 6 has a concave spherical ball for mounting and coupling the load device 1 to the load stamp 2. The spring element 7 is composed of pre-stressed disk springs. The load stamp 2 includes a stamp shaft 9 and a stamp head 10. A support plate 11 with a spherical ball is formed on the stamp head 10. The spherical ball arranged on the support plate 11 is convex and has a shape and size designed to correspond to those of the spherical ball formed in the detachable cap 6. An acceleration sensor 12 and a radio module 13 are arranged in the stamp head 10. The face of the stamp shaft 9 facing away from the stamp head 10 forms a stamp face 14. The load stamp 2 is essentially cylindrical. The stamp face 14 is a circular surface. The guide member 3 includes a cylindrical guide sleeve 15 having a longitudinal axial through opening 16 for guiding the stamp shaft 9 and a support plate 17 with a support surface 18, wherein the through opening 16 continues through the support plate 17 and forms an opening in the support surface 18. A displacement sensor 19 and a radio module 20 are arranged on the end of the guide sleeve 15 facing away from the support plate 17.

FIG. 2 shows a prepared field testing apparatus for determining the dynamic elastic modulus $E_d$ of asphalt applied as an asphalt layer 21 to a base layer 22. Compacted soil 23 is located underneath the base layer 22.

The support plate 17 rests with its support surface 18 flat on the asphalt surface 24 to be tested, i.e. on the surface of the asphalt layer 21. The stamp shaft 9 of the load stamp 2 is inserted far enough into the through-opening 16 of the guide sleeve 15 so that its stamp face 14 also rests flat on the asphalt surface 24 to be tested. The load stamp 2 is freely movable within the guide sleeve 15 in the longitudinal axial direction. The load device 1 is attached with its detachable cap 6 on the support plate 11 of the load stamp 2, such that the two corresponding spherical cavities of the detachable cap 6 and of the support plate 11 positively mesh. The guide rod 4 is oriented approximately vertically. The drop weight 8 is in a raised position and is held in this position by the release mechanism 5. The exact position was determined in preliminary experiments and was set so that the drop weight 8 is accelerated after release due to the action of the gravitational force $F_s$ in free fall so as to produce, upon impact on the spring element 7, a force impact of the load device 1 on the load stamp 2 with a force of 6.28 kN.

In the test procedure, the release mechanism 4 is actuated and the drop weight 8 is unlatched, i.e. released. The drop weight 8 drops substantially vertically downward, due to the effect of the gravitational force $F_s$ and guided by the guide rod 4, and strikes the spring element 7 with an energy predetermined by the mass of the drop weight 8 and the drop height. The generated force impact is introduced into the detachable cap 6 via the spring element 7 and therefrom transmitted to the load stamp 2 by way of the positive engagement of the corresponding spherical balls of the releasable element 6 and the support plate 11, and is transmitted by the load stamp 2 via the stamp face 14 to the asphalt to be tested. As a result of the force impact, the stamp shaft 9 of the load stamp 2 penetrates the asphalt, causing an elastic deformation and sometimes a permanent deformation of the asphalt. The time dependence of the acceleration of the load stamp 2 is measured with the acceleration sensor 12 and transmitted via the radio module 13 to an unillustrated electronic evaluation unit and temporarily stored therein. The movement of the load stamp 2 is measured with the displacement sensor 19 and is also transmitted to the electronic evaluation unit via the radio module 20 and temporarily stored.

The static penetration depth $s_{st}$ of the stamp shaft 9 of the load stamp 2 into the asphalt to be tested is determined from the movement of the load stamp 2, wherein the static depth $s_{st}$ refers to the penetration depth of the stamp shaft 9 into the asphalt to be tested, in which the stamp shaft 9 remains after the force impact has subsided. The static penetration depth $s_{st}$ therefore describes permanent deformation of the asphalt layer 21 caused by the force impact of the stamp shaft 9. The measured static penetration depth $s_{st}$ is compared with a predetermined minimum static penetration depth $s_{stmin}$. If the measured static penetration depth $s_{st}$ is greater than the predetermined minimum static penetration depth $s_{stmin}$, an additional force impact is generated without changing the position of the support plate 18 on the asphalt surface 24, and introduced at the same location into the asphalt to be tested. To this end, the drop weight 8 is moved against the force of gravity $F_s$ along the guide rod 4 and is positioned with the release device 5. The guide rod 4 is oriented approximately vertically and the release device 5 is actuated. A force impact is generated, as described above, and introduced into the asphalt to be tested via the stamp shaft 9 of the load stamp 2. The time dependence of the acceleration of the load stamp 2 due to this force impact is measured and transmitted to the electronic evaluation unit and temporarily stored. The movement of the load stamp 2 is also recorded and transmitted to the electronic evaluation unit. The static penetration depth $s_{st}$ of the stamp shaft 9 caused by this force impact is determined and compared with the predetermined minimum static penetration depth $s_{stmin}$. As described above, additional force impacts are generated with the load device 1 and introduced into the asphalt to be tested via the stamp shaft 9 of the load stamp 2, and the time dependence of the acceleration and the movement of the load stamp 2 are measured and temporarily stored, and the static penetration depth $s_{st}$ of the stamp shaft 9 is determined from the movement of the load stamp 2, until the determined static penetration depth $s_{st}$ of the stamp shaft 9 is smaller than the predetermined is minimum static penetration depth $s_{stmin}$. The time dependence of the penetration depth s of the stamp shaft 9 of the load stamp 2 into the asphalt to be tested is then determined by a two-time integration from the temporarily stored time dependence of the acceleration caused by the last force impact that produced a static penetration depth $s_{st}$ smaller than or equal to the predetermined minimum static penetration depth $s_{stmin}$, and the total penetration depth $s_{tot}$ is determined from the maximum value.

FIG. 3a shows a curve of the measured time dependence of the acceleration of the load stamp (2), wherein the stamp face (12) of the load stamp (2) is circular with a diameter of 30 mm, a force impact of 6.28 kN acting on the load stamp (2) is produced by the load device (1), and the temperature of the asphalt layer (21) is about 50° C.

FIG. 3b shows a curve of the time dependence of the penetration depth s of the stamp shaft 9 of the load stamp 2 in the asphalt to be tested determined by a two-time integration of the time dependence of the acceleration of the load shaft 9 of the load stamp 2. The maximum value of this curve is the total penetration depth $s_{tot}$, which in the actual situation depicted in FIGS. 3a and 3b is $s_{tot}$=0.35 mm. The calculated static penetration depth $s_{st}$ is $s_{st}$=0.9 mm, wherein the predetermined minimum static penetration depth is $s_{stmin}$=0.1 mm. The dynamic penetration depth $s_{dyn}$ is calculated from the equation $s_{dyn}=s_{tot}-s_{st}$ and has a calculated value of $s_{dyn}$=0.26 mm.

The dynamic elastic modulus $E_d$ can then be calculated using the following values: force impact F=6.28 kN, radius r of the stamp face r=15 mm, and the Poisson ratio for asphalt μ=0.25, according to the equation $$E_d = 2*(1-\mu^2)*F/\Pi*r*s_{dyn}.$$

The calculated value for the dynamic elastic modulus $E_d$ is 950 MN/m².

The dynamic elastic modulus $E_d$ of asphalt, which is applied as an asphalt layer 21 on a base layer 22, can be easily determined with the aforedescribed field testing apparatus and according to the aforedescribed method directly on site. This is important, for example, in the construction of new roadways to determine the compaction of the asphalt attained when installing the asphalt layer 21.

LIST OF REFERENCE SYMBOLS 1 load device
2 load stamp
3 guide element
4 guide rod
5 release device
6 detachable cap
7 spring element
8 drop weight
9 stamp shaft
10 stamp head
11 support plate
12 Acceleration sensor
13 Radio Module
14 stamp face
15 guide sleeve
16 Through opening
17 support plate
18 support surface
19 displacement sensor
20 Radio Module
21 asphalt layer
22 base layer
23 compacted soil
24 asphalt surface
$E_d$ dynamic elastic modulus
$F_s$ gravitational force
s penetration depth
$s_{dyn}$ dynamic penetration depth
$s_{tot}$ total penetration depth
$s_{st}$ static penetration depth
$s_{stmin}$ minimum static penetration depth

The invention claimed is:

1. A field testing apparatus for determining dynamic elastic modulus of asphalt, comprising:
    a load device (1) including:
        a guide rod (4),
        a release device (5) attached to one end of the guide rod (4),
        a detachable cap (6) attached to an opposite end of the guide rod (4),
        a drop weight (8) guided by the guide rod (4),
        a spring element (7); wherein prior to disengagement of the drop weight (8) by the release device (5), the spring element (7) rests on the detachable cap (6) while the drop weight (8) is separated a predetermined distance from the spring element (7),
    a load stamp (2) having a substantially cylindrical stamp shaft (9) terminating at one end with a stamp face (14) and a stamp head (10) formed on its opposite end; wherein formed on the stamp head (10) is a support plate (11) non-positively coupling the load device (1) to the load stamp (2); the load stamp (2) further including an acceleration sensor (12) for measuring time dependence of acceleration of the load stamp (2),
    a guide element (3) having a longitudinal axial through opening (16) extending from a support surface (18) on one end to an opposite terminating end, the stamp shaft (9) being passable via the longitudinal axial through opening (16) past the support surface (18); arranged on the guide element is a displacement sensor (19) for measuring movement of the load stamp (2).

2. The field testing apparatus according to claim 1, wherein a support plate (17) is arranged on one end of the guide element (3), wherein the support plate (17) includes a support surface (18) and the support plate (17) is oriented perpendicular to a longitudinal axis of the guide element (3).

3. The field testing apparatus according to claim 1, wherein the guide element (3) comprises a circular-cylindrical guide sleeve (15) and the load stamp (2) comprises a circular-cylindrical stamp shaft (9) with a circular stamp face (14), and the stamp shaft (9) is insertable into the guide sleeve (15) so as to freely move in a longitudinal direction.

4. The field testing apparatus according to claim 3, wherein the stamp face (14) of the load stamp (2) has a diameter of 10 mm to 60 mm, the drop weight (8) has a mass of about 8 kg to about 20 kg, and a drop height of the drop weight (8) determined by a length of the guide rod (4) and position of the release device (5) on the guide rod (4) are selected so that the drop weight (8) acts on the load stamp (2) with a three of about 5 kN to about 15 kN.

5. The field testing apparatus according, to claim 3, wherein
    the stamp face (14) of the load stamp (2) has a diameter of about 30 mm, the drop weight (8) has a mass about 10 kg, and the drop height of the drop weight (8) determined by the length of the guide rod (4) and the position of the release device (5) on the guide rod (4) are selected so that the drop weight (8) acts on the load stamp (2) with a force of about 6.28 kN.

6. The field testing apparatus according to claim 3, wherein the drop weight (8) does not travel along the stamp shaft (9).

7. The field testing apparatus according to claim 1, wherein the displacement sensor (19) and the acceleration sensor (12) are connected to a radio module (13, 20) for transmitting measured values to an electronic evaluation device.

8. The field testing apparatus according to claim 1, wherein the drop weight (8) is movable independently of the spring element (7).

9. A method for determining dynamic elastic modulus of asphalt using a field testing apparatus, comprising at least the steps of:
    a) placing a support surface (18) of a support plate (11) associated with a guide element (3) on an asphalt surface (24) to be tested and inserting a stamp shaft (9) of a load stamp (2) into the guide element (3), such that the stamp face (14) rests on the asphalt surface (24) to be tested,
    b) fricitionally coupling of a load device (1) to the load stamp (2) by placing the detachable cap (6) associated with the load device (1) on the support plate (11),
    c) positioning of a drop weight (8) by raising the drop weight against an action of gravitational force ($F_s$) and locking the drop weight (8) in a raised position with a release device (5) and aligning a guide rod (4) associated with the load device (1) in an approximately vertical orientation, and d) generating a force impact by releasing of the drop weight (8), e) measuring and temporarily storing time dependence of acceleration of the load stamp (2) with an acceleration sensor (12) and movement of the load stamp (2) with a displacement sensor (19), f) in a step preceding the process step a), the temperature of the asphalt to be tested is adjusted to between 40° C. and 60° C., g) the steps c) through e) are cyclically repeated, wherein in each cycle a static penetration depth ($s_{st}$) of the stamp shaft (9) of the load stamp (2) into the asphalt to be tested caused by the respective force impact is determined from the movement of the load stamp (2), and the repeated cycling through the process steps c) through e) is terminated upon reaching or falling below a predetermined minimum penetration depth ($s_{stmin}$) as a result of a force impact, a total penetration depth ($s_{ges}$) of the stamp shaft (9) of the load stamp (2) into the asphalt to be tested is determined from the measured and temporarily stored time dependence of acceleration of the load stamp (2) caused by the force impact by a two-time integration and subsequent formation of a maximum value, a dynamic penetration depth ($s_{dyn}$) is calculated from the determined total penetration depth ($s_{ges}$) and the static penetration depth ($s_{st}$) for this force impact by using the equation $s_{dyn} = s_{tot} - s_{st}$, and h) the dynamic of elastic modulus ($E_d$) is determined from the dynamic penetration depth ($s_{dyn}$).

10. The method according to claim 9, wherein the dynamic elastic modulus ($E_d$) is determined with the equation $$E_d = 2 - (1-\mu^2) - F/\Pi * r * s_{dyn}$$

with
$\mu$=Poisson ratio for asphalt=0.25
F=force impact
r=radius of the stamp face.

11. The method according to claim 10, wherein the predetermined minimum static penetration depth ($s_{st\,min}$) caused by a force impact, where the cyclic repetition of the steps c) to e) is terminated, is ≤0.15 mm, preferably ≤0.1 mm.

12. The method according to claim 9, wherein prior to disengagement of the drop weight (8) by the release device (5) in step d), a spring element (7) rests on the detachable cap (6) while the drop weight (8) is separated a predetermined distance from the spring element (7).

13. The method according to claim 12, wherein the drop weight (8) is movable independently of the spring element (7).

14. The method according to claim 9, wherein the drop weight (8) does not travel along the stamp shaft (9).

* * * * *

UNITED STATES PATENT AND TRADEMARK OFFICE
CERTIFICATE OF CORRECTION

PATENT NO. : 9,228,927 B2
APPLICATION NO. : 13/851578
DATED : January 5, 2016
INVENTOR(S) : Bernd Zorn Page 1 of 1

It is certified that error appears in the above-identified patent and that said Letters Patent is hereby corrected as shown below:

Claims section:

Column 8, Claim 9, line 9, change "fricitionally" to --frictionally--.

Signed and Sealed this
Fifth Day of July, 2016

Michelle K. Lee
*Director of the United States Patent and Trademark Office*